United States Patent
Kawase et al.

(10) Patent No.: US 6,182,659 B1
(45) Date of Patent: Feb. 6, 2001

(54) VIRUS-REMOVING FILTER

(75) Inventors: Mitsuo Kawase, Chita; Yuji Kawase, Handa; Kazunari Yamada, Nagoya; Yasuo Suzuki, Shizuoka, all of (JP)

(73) Assignee: NGK Insulators, Ltd. (JP)

( * ) Notice: Under 35 U.S.C. 154(b), the term of this patent shall be extended for 0 days.

(21) Appl. No.: 09/093,790

(22) Filed: Jun. 9, 1998

(30) Foreign Application Priority Data

Jun. 16, 1997 (JP) .................................................. 9-158388

(51) Int. Cl.$^7$ ...................................................... A62B 18/02
(52) U.S. Cl. ................................................................ 128/206.18
(58) Field of Search .................... 128/206.18; 210/500.3, 210/644–647; 514/832

(56) References Cited

U.S. PATENT DOCUMENTS 4,295,343 * 10/1981 Izumi ...................................... 62/309
4,857,196 * 8/1989 Manabe et al. .................... 210/500.3

* cited by examiner

Primary Examiner—Michael A. Brown
Assistant Examiner—Lalita M. Hamilton

(57) ABSTRACT

A virus-removing filter using, as a virus-capturing body, at least one kind of *Streptococcus agalactiae* type II culture and Type II polysaccharide.

10 Claims, 3 Drawing Sheets

Glc : glucose
Gal : galactose
GlcNAc : N-acetyl glucosamine
NeuNAc : Silalic acid

VIRUS-REMOVING FILTER

BACKGROUND OF THE INVENTION (1) Field of the Invention

The present invention relates to a filter capable of removing viruses such as influenza.

(2) Related Art Statement

As a means for removing the virus suspended in the air, a technique has been conventionally known to capture the virus with a filter and inactivate the thus captured virus with ultraviolet light. However, since the ultraviolet light is harmful against the human bodies, it is difficult to use such a technique in ordinary living spaces. In addition, the ultraviolet light is likely to deteriorate the material of the filter and any accompanying equipment. Further, although gauze masks are widely used in the ordinary living spaces to cope with the viruses such as influenza, such gauze masks cannot capture the viruses.

SUMMARY OF THE INVENTION

The present invention is directed to solving the above-mentioned conventional problem, and has been accomplished to provide virus-removing filters which can be used in the ordinary living space and effectively remove the viruses such as influenza virus.

The present invention has been accomplished to attain the above object.

A first aspect of the present invention is to provide a virus-removing filter using, as a virus-capturing body, at least one kind of *Streptococcus agalactiae* type II culture and Type II polysaccharide.

A second aspect of the present invention is to provide a virus-removing filter using, as a virus-capturing body, a substrate in which at least one kind of *Streptococcus agalactiae* type II culture and Type II polysaccharide is impregnated or kneaded.

removing filter using, as a virus-capturing body, a material with which at least one kind of *Streptococcus agalactiae* type II culture and Type II polysaccharide is covalently bonded.

A fourth aspect of the present invention is to provide a virus-removing filter using, as a virus-capturing body, a polymerized/copolymerized material that is obtained by polymerizing and/or which at least one kind of *Streptococcus agalactiae* type II culture and Type II polysaccharide is incorporated.

These and other objects, features and advantages of the invention will be appreciated upon reading of the following description of the invention when taken in conjunction with the attached drawings, with the understanding that some modifications, variations and changes of the same could be easily made by the skilled person in the art to which the invention pertains.

BRIEF DESCRIPTION OF THE INVENTION

For a better understanding of the invention, reference is made to the attached drawings, wherein.

DETAILED DESCRIPTION OF THE INVENTION

In the following, embodiments of the preset invention will be explained in more detail.

(1) In order to capture the viruses, the filter according to the present invention uses, at least one kind of Streptococcus agalactiae type II culture, *Streptococcus agalactiae* type II polysaccharide, and the covalently bonded material and the polymer thereof.

*Streptococcus agalactiae* ("B-group Streptococcus") type II culture is available as ATTC (American Type Culture Collection) No. 27451. The *Streptococcus agalactiae* type II polysaccharide is a polysaccharide present at a surface layer of the *Streptococcus agalactiae* culture. As to the *Streptococcus agalactiae* culture, see (Harold J. Jennings et al., "Structure Determination of the Capsular Polysaccharide Antigen of Type II Group B Streptococcus", J. Biol. Chem. 1998, vol. 258, No. 3, 1793–1798.

Figure 1:
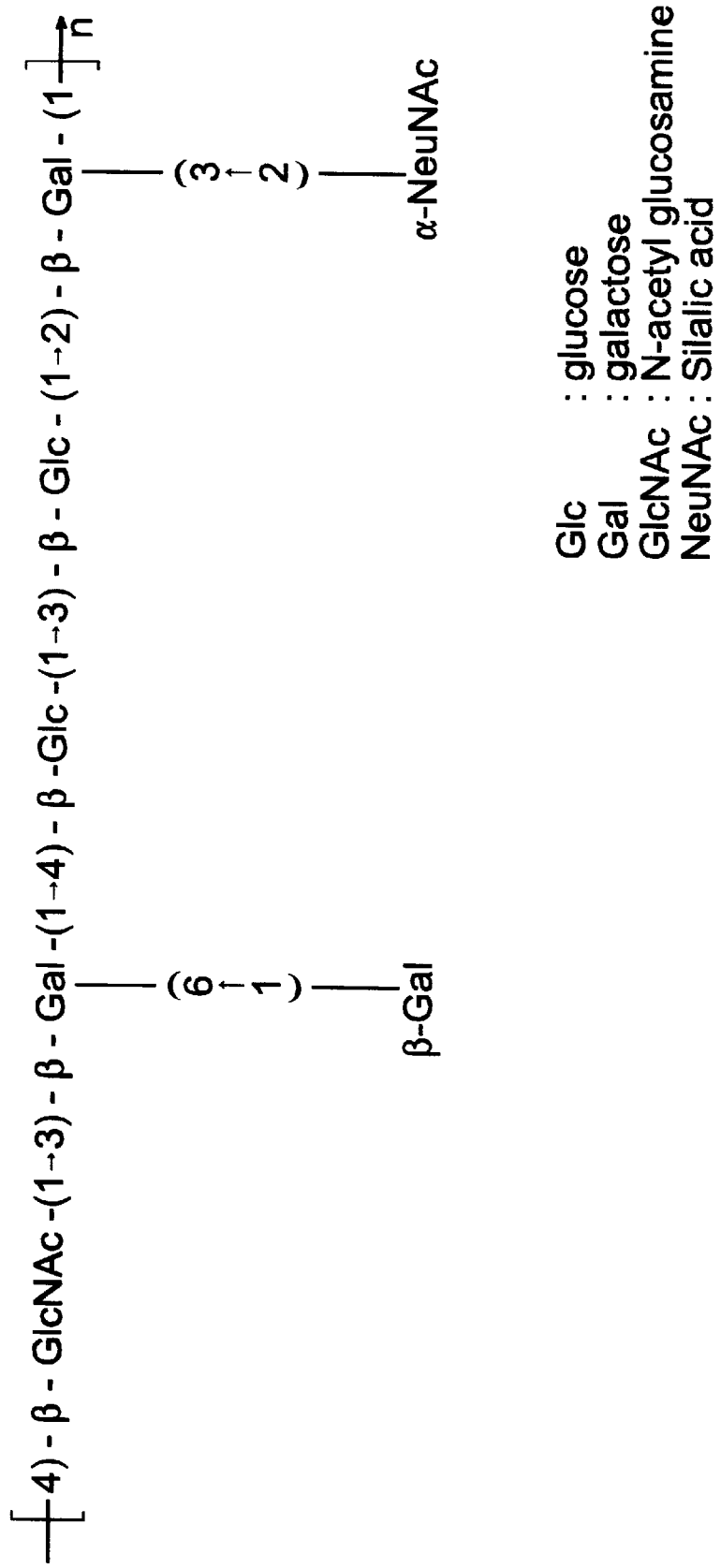
FIG. 1 shows the molecular structures of *Streptococcus agalactiae* type II polysaccharide (containing sialic acid)
Figure 2:
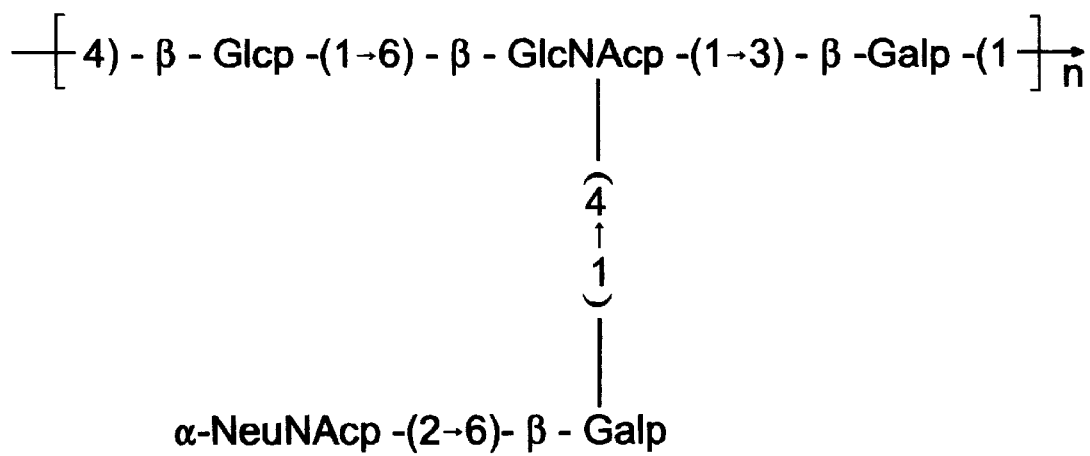
FIG. 2 shows a the molecular structures of *Streptococcus agalactiae* type III polysaccharide (containing sialic acid) used as comparative examples in Experiments 5 and 6.
Figure 3:
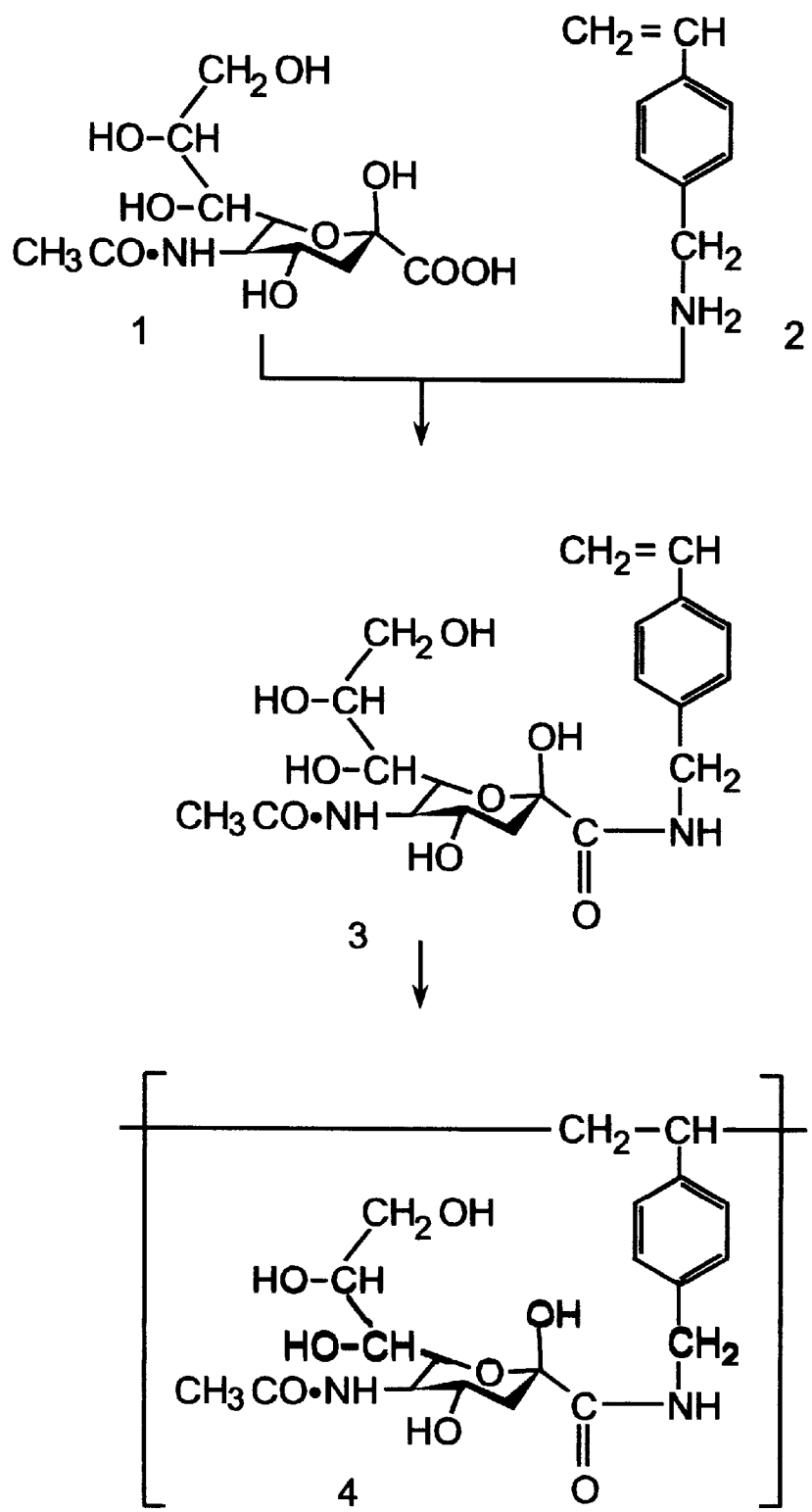
FIG. 3 is a chemical reaction flow chart of the steps of producing a composite glucocide polymeric material containing sialic acid.

FIGS. 1 and 2 show the *Streptococcus agalactiae* type II polysaccharide used in the present invention and the *Streptococcus agalactiae* type III polysaccharide used as comparative examples On the other hand, many viruses such as influenza to be captured by the present invention have proteins called "hemagglutinin" at their surfaces. It is known that as this hemaggultinin bonds to sialic acid at surfaces of cells of an animal, the animal is infected with such viruses. That is, these viruses function to infect the cells via sialic acid as receptor at the cell surfaces of the animal. The present invention utilizes the above phenomenon, and is to remove the virus having the "hemaggultinin" by capturing the virus with the filter in which *Streptococcus agalactiae* type II culture and/or Type II polysaccharide containing sialic acid is incorporated as the virus-capturing body.

(2) At least one of the *Streptococcus agalactiae* type II culture and Type II polysaccharide can be used as the virus-removing body in the form of the substrate in which at least one of the *Streptococcus agalactiae* type II culture and Type II polysaccharide is impregnated or kneaded. If a gauze is used as the substrate, it may be used as a virus-removing mask.

(3) The material with which at least one of the *Streptococcus agalactiae* type II culture and Type II polysaccharide is covalently bonded may be used as the virus-capturing body. In this case, when the covalently bonded material is held between gauzes, it may be also used as a virus-removing mask.

(4) The polymerized/copolymerized material which is obtained by polymerizing and/or copolymerizing styrene monomer and/or acryl amide monomer into which at least one kind of *Streptococcus agalactiae* type II culture and Type II polysaccharide is incorporated may be used as the virus-capturing body. FIG. 3 is a flow chart for illustrating the steps of producing such a polymerized material by using the styrene monomer. For simplification, only a sialic acid group is shown as "1". The sialic acid residual group and p-vinylbenzyl amine 2 are subjected to a condensation reaction, thereby obtaining a styrene monomer substituted by the sialic acid residue as shown by 3. The substituted styrene monomer is polymerized, thereby obtaining a complex polysaccharide polymer 4. According to this process, since the sialic acid or the like can be bonded to the synthetic resin, the resulting synthetic resin can be used as a virus-removing filter or a virus-removing mask in the state that the synthetic resin is used as it is or in a form in which the synthetic resin is held between gauze. If the synthetic resin is used as it is, a synthetic resin having gas permeability may be used. If the synthetic resin is used in the state that the resin is held between the gauze, the synthetic resin can used in the form of powder, and held in a gas-permeable bag, and the bag is sandwiched with gauze.

(Experiment 1)

*Streptococcus agalactiae* (hereinafter referred to as B-group Streptococcus "GBS") Type II strain (ATCC27541) was cultivated in a Todd-Hewitt broth containing 2% glucose and 1.5% disodium hydrogenphosphate and buffered at pH 7.0 to 7.2. A component of the type II polysaccharide shown in FIG. 1 was separated and extracted from the resulting culture, and was dissolved into pure water, thereby preparing a 1 % aqueous solution. A conventional filter (a commercially available gauze mask) was immersed in this aqueous solution, lightly dewatered, and dried to attach the extracted component thereon. Thus, the filter with the sugar containing sialic acid (hereinafter referred to as "sialic acid-containing filter 1") was obtained. Virus-removing tests were conducted by using this sialic acid-containing filter 1 and a conventional filter. Test results were examined by comparison together with that of a filter 2 in a case of GBS Type III.

The test was conducted as follows. That is, a suspended liquid was prepared by suspending A type influenza virus A/Memphis/1/85 (H3N2) strain in physiologic saline. Then, the suspended liquid was passed through each of filters, and a titer of the liquid passed was measured. The titer was measured by utilizing a phenomenon that if influenza virus attached to red blood cells, the cells cause aggregation. That is, 2-fold diluted, 4-fold diluted, 8-fold diluted, . . . aqueous solutions were prepared by diluting the suspended liquid having passed the filter with physiologic saline. A given amount of each of the thus diluted aqueous solutions was successively mixed with the same amount of a 0.4% suspended liquid of fowl red blood cells, and the titer was obtained by determining up to which fold diluted solution the fowl red blood cell aqueous solution caused aggregation reaction. Results are shown in the following Table 1. In this table, blank shows a titer of a raw liquid (the virus-suspended liquid before dilution).

TABLE 1

| Kind of filter | Titer |
|---|---|
| Blank | 1024 |
| Conventional filter (one sheet) | 1024 |
| Conventional filter (two sheets) | 1024 |
| Filter 2 (GBS Type III) (one sheet) | 64 |
| Filter 2 (GBS Type III) (two sheet) | 16 |
| Filter 1 (GBS Type II) (one sheet) | 16 |
| Filter 1 (GBS Type II) (two sheet) | 8 |

As is clear from the data shown in Table 1, the titer of the liquid having passed each of the conventional filters was the same as that of the raw liquid, and the conventional filters had completely no virus-removing effect. To the contrary, the titers of the liquid having passed each of the filters according to the present invention were reduced to 1/16 to 1/64 of that of the raw liquid, which exhibited the virus-removing effect of the filters according to the present invention. As compared with the GBS Type III filters, the filters 1 using the GBS Type II polysaccharide had the titers reduced to ¼ to ½, and thus exhibited stronger virus-removing power.

(Experiment 2)

*Streptococcus agalactiae* (hereinafter referred to as B-group Streptococcus "GBS") Type II strain (ATCC27541) was cultivated in a Todd-Hewitt broth containing 2% glucose and 1.5% disodium hydrogenphosphate and buffered at pH 7.0 to 7.2. After the cultivated liquid was subjected to centrifugal separation, the resulting solid component was washed twice or three times with physiologic saline. Thereafter, the washed culture was suspended in pure water, thereby preparing a 1% suspended liquid. A conventional filter (a commercially available gauze mask) was immersed in this aqueous solution, lightly dewatered, and dried to attach the extracted component thereon. Thus, the filter containing the GBS Type II (hereinafter referred to as "filter 3") was obtained. Virus-removing tests were conducted by using this sialic acid-containing filter 3 and a conventional filter. Test results were examined by comparison together with that of a filter 4 in a case of GBS Type III.

The test was conducted as follows. That is, a suspended liquid was prepared by suspending A type influenza virus A/Memphis/1/85 (H3N2) strain in physiologic saline. Then, the suspended liquid was passed through each of filters, and a titer of the liquid passed was measured. The titer was measured by utilizing a phenomenon that if influenza virus attached to red blood cells, the cells cause aggregation. That is, 2-fold diluted, 4-fold diluted, 8-fold diluted, . . . aqueous solutions were prepared by diluting the suspended liquid having passed the filter with physiologic saline. A given amount of each of the thus diluted aqueous solutions was successively mixed with the same amount of a 0.4% suspended liquid of fowl red blood cells, and the titer was obtained by determining up to which fold diluted solution the fowl red blood cell aqueous solution caused aggregation reaction. Results are shown in the following Table 2. In this table, blank shows a titer of a raw liquid (the virus-suspended liquid before dilution).

TABLE 2

| Kind of filter | Titer |
|---|---|
| Blank | 1024 |
| Conventional filter (one sheet) | 1024 |
| Conventional filter (two sheets) | 1024 |
| Filter 4 (GBS Type III) (one sheet) | 32 |
| Filter 4 (GBS Type III) (two sheet) | 8 |
| Filter 3 (GBS Type II) (one sheet) | 8 |
| Filter 3 (GBS Type II) (two sheet) | 4 |

As is clear from the data shown in Table 2, the titer of the liquid having passed each of the conventional filters was the same as that of the raw liquid, and the conventional filters had completely no virus-removing effect. To the contrary, the titers of the liquid having passed each of the filters according to the present invention were reduced to 1/32 to 1/128 of that of the raw liquid, which exhibited the virus-removing effect of the filters according to the present invention. As compared with the GBS Type III filters, the filters 1 using the GBS Type II polysaccharide had the titers reduced to ¼ to ½, and thus exhibited stronger virus-removing power.

(Effects of the Invention)

As explained above, according to the present invention, since at least one kind of *Streptococcus agalactiae* type II culture and Type II polysaccharide is used as it is or they are or as covalently bonded, polymerized or copolymerized is used as the virus-capturing body, the virus can be effectively removed. In addition, since *Streptococcus agalactiae* type II culture and Type II polysaccharide are contained in the human cells, they are harmless so that the virus-removing filter according to the present invention can be advantageously used with safe even in the ordinary living space.

What is claimed is:

1. A virus-removing filter comprising, a virus-capturing body containing at least one kind of *Streptococcus agalactiae* type II culture and Type II polysaccharide.

2. A virus-removing filter of claim 1, wherein the virus-capturing body is a substrate in which at least one kind of *Streptococcus agalactiae* type II culture and Type II polysaccharide is impregnated or kneaded.

3. A virus-removing filter of claim 2, wherein the filter is to remove air-suspended virus from air, and the substrate allows air to pass therethrough.

4. A virus-removing filter of claim 3, wherein the substrate has a shape permitting the filter material to be placed over the nose of a wearer.

5. A virus-removing filter of claim 1, wherein the virus-capturing body is a material with which at least one kind of *Streptococcus agalactiae* type II culture and Type II polysaccharide is covalently bonded.

6. A virus-removing filter of claim 5, wherein the filter is to remove air-suspended virus from air, and the material allows air to pass therethrough.

7. A virus-removing filter of claim 6, wherein the substrate has a shape permitting the filter material to be placed over the nose of a wearer.

8. A virus-removing filter of claim 1, wherein the virus-capturing body is a polymerized/copolymerized material which is obtained by polymerizing and/or copolymerizing styrene monomer and/or acryl amide monomer into which at least one kind of *Streptococcus agalactiae* type II culture and Type II polysaccharide is incorporated.

9. A virus-removing filter of claim 8, wherein the filter is to remove air-suspended virus from air, and the polymerized/copolymerized material allows air to pass therethrough.

10. A virus-removing filter of claim 9, wherein the material has a shape permitting the filter material to be placed over the nose of a wearer.

* * * * *